United States Patent
Lu et al.

(10) Patent No.: US 10,351,914 B2
(45) Date of Patent: *Jul. 16, 2019

(54) BIOMARKERS FOR PIN1-ASSOCIATED DISORDERS

(71) Applicant: Beth Israel Deaconess Medical Center, Inc., Boston, MA (US)

(72) Inventors: Kun Ping Lu, Newton, MA (US); Xiao Zhen Zhou, Newton, MA (US); Shuo Wei, Chestnut Hill, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/326,981

(22) PCT Filed: Jul. 16, 2015

(86) PCT No.: PCT/US2015/040771
§ 371 (c)(1),
(2) Date: Jan. 17, 2017

(87) PCT Pub. No.: WO2016/011265
PCT Pub. Date: Jan. 21, 2016

(65) Prior Publication Data
US 2017/0204466 A1    Jul. 20, 2017

Related U.S. Application Data

(60) Provisional application No. 62/025,588, filed on Jul. 17, 2014.

(51) Int. Cl.
| | | |
|---|---|---|
| *A61K 9/00* | (2006.01) | |
| *A61K 9/06* | (2006.01) | |
| *A61K 31/203* | (2006.01) | |
| *C12Q 1/6883* | (2018.01) | |
| *C12Q 1/6886* | (2018.01) | |

(52) U.S. Cl.
CPC .......... *C12Q 1/6886* (2013.01); *A61K 9/0019* (2013.01); *A61K 9/06* (2013.01); *A61K 31/203* (2013.01); *C12Q 1/6883* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,223,409 A | 6/1993 | Ladner et al. |
| 5,283,317 A | 2/1994 | Saifer et al. |
| 5,459,039 A | 10/1995 | Modrich et al. |
| 5,498,531 A | 3/1996 | Jarrell |
| 5,952,467 A | 9/1999 | Hunter et al. |
| 5,972,697 A | 10/1999 | Hunter et al. |
| 6,462,173 B1 | 10/2002 | Lu et al. |
| 6,495,376 B1 | 12/2002 | Lu et al. |
| 6,596,848 B1 | 7/2003 | Hunter et al. |
| 6,649,611 B2 | 11/2003 | Blumberg et al. |
| 6,764,698 B1 | 7/2004 | Byun et al. |
| 7,125,677 B2 | 10/2006 | Hunter et al. |
| 7,125,955 B2 | 10/2006 | Hunter et al. |
| 7,148,003 B2 | 12/2006 | Hunter et al. |
| 7,161,060 B1 | 1/2007 | Duff et al. |
| 7,164,012 B2 | 1/2007 | Hunter et al. |
| 7,175,830 B2 | 2/2007 | Collins et al. |
| 7,592,145 B2 | 9/2009 | Bao et al. |
| 8,129,131 B2 | 3/2012 | Lu et al. |
| 8,258,099 B2 | 9/2012 | Lu et al. |
| 8,771,693 B2 | 7/2014 | Lu et al. |

(Continued)

FOREIGN PATENT DOCUMENTS

| | | |
|---|---|---|
| JP | 2004-532390 A | 10/2004 |
| WO | WO-94/10300 A1 | 5/1994 |

(Continued)

OTHER PUBLICATIONS

Anderson et al, Nucleic Acids Research, 2010, vol. 38, pp. 5884-5892 (Year: 2010).*
Hall et al, Immunity, 2011, vol. 35, pp. 13-22 (Year: 2011).*
Alizadeh et al, International Immunopharmacology, 2014, vol. 18, pp. 43-49 (Year: 2014).*
Eswaran et al., "Crystal structures and inhibitor identification for PTPN5, PTPRR and PTPN7: a family of human MAPK-specific protein tyrosine phosphatases," Biochem J. 395(3):483-91 (2006).
Notice of Reasons for Rejection and English Translation for Japanese Patent Application No. 2015-516246, dated Mar. 28, 2017 (12 pages).
U.S. Appl. No. 61/490,338, Lu et al.
U.S. Appl. No. 61/968,862, Lu et al.

(Continued)

*Primary Examiner* — Karen A. Canella
(74) *Attorney, Agent, or Firm* — Clark & Elbing LLP

(57) ABSTRACT

Biomarkers and driver mutations for diagnosis and prognosis of Pin 1-associated diseases are disclosed. In one embodiment, the methods for diagnosis of Pin 1-associated diseases may include detecting the level of Pin1 to stage abnormal cell growth, such as breast or prostate cancer. In another embodiment, the methods include evaluating the efficacy of a treatment of abnormal cell growth, such as cancer, by monitoring the levels of Pin1. In another embodiment, the methods include using driver mutations to determine the pharmacogenetics of abnormal cell growth, such as cancer. In the present disclosure, elevated active monomeric Pin1 levels may be detected by Pin1 biomarkers, which may include Pin1 Q33K or E100D driver mutations, Pin1 protein or transcript overexpression, dephosphorylation of Pin1 on Ser71, dephosphorylation of S16, phosphorylation of S65, phosphorylation of S138, deacetylation of Pin1 on K13 and deacetylation of K46, and/or desumoylation of Pin1 on K6 and desumolation of K63, among others.

26 Claims, 3 Drawing Sheets

(56) References Cited

U.S. PATENT DOCUMENTS

| | | | |
|---|---|---|---|
| 2002/0002552 | A1 | 1/2002 | Schultz et al. |
| 2002/0025521 | A1 | 2/2002 | Lu et al. |
| 2002/0106348 | A1 | 8/2002 | Huang et al. |
| 2004/0176912 | A1 | 9/2004 | Sowadski et al. |
| 2005/0159485 | A1 | 7/2005 | Jost-Price et al. |
| 2005/0239095 | A1 | 10/2005 | Lu et al. |
| 2005/0250742 | A1 | 11/2005 | Dagostino et al. |
| 2006/0018899 | A1 | 1/2006 | Kao et al. |
| 2006/0074222 | A1 | 4/2006 | Lu et al. |
| 2007/0072875 | A1 | 3/2007 | McMaster |
| 2007/0203236 | A1 | 8/2007 | Smith et al. |
| 2008/0118505 | A1 | 5/2008 | Tedder |
| 2008/0214470 | A1 | 9/2008 | Lu et al. |
| 2008/0248043 | A1 | 10/2008 | Babcook et al. |
| 2009/0053209 | A1 | 2/2009 | Malter et al. |
| 2009/0105249 | A1 | 4/2009 | Benjamin et al. |
| 2009/0258352 | A1 | 10/2009 | Lu et al. |
| 2010/0010084 | A1 | 1/2010 | Yu |
| 2010/0278832 | A1 | 11/2010 | Kamogawa et al. |
| 2011/0034554 | A1 | 2/2011 | Washington |
| 2011/0039278 | A1* | 2/2011 | Pieribone ............... G01N 33/53 435/7.21 |
| 2011/0065704 | A1 | 3/2011 | Ryder |
| 2011/0077250 | A1 | 3/2011 | Ryder |
| 2011/0104756 | A1 | 5/2011 | Rodriguez et al. |
| 2011/0206691 | A1* | 8/2011 | Mosse .................. C12Q 1/6886 424/158.1 |
| 2012/0183560 | A1 | 7/2012 | Akassoglou |
| 2013/0028900 | A1 | 1/2013 | Lu et al. |
| 2014/0086909 | A1 | 3/2014 | Lu et al. |
| 2014/0219957 | A1 | 8/2014 | Lu et al. |
| 2014/0242100 | A1 | 8/2014 | Lu et al. |
| 2015/0044278 | A1 | 2/2015 | Lu et al. |
| 2015/0133442 | A1 | 5/2015 | Lu et al. |

FOREIGN PATENT DOCUMENTS

| | | |
|---|---|---|
| WO | WO-94/16101 A2 | 7/1994 |
| WO | WO-97/17986 A1 | 5/1997 |
| WO | WO-99/09969 A1 | 3/1999 |
| WO | WO-02/064015 A2 | 8/2002 |
| WO | WO-02/065091 A2 | 8/2002 |
| WO | WO-02/092765 A2 | 11/2002 |
| WO | WO-03/073999 A2 | 9/2003 |
| WO | WO-2004/016751 A2 | 2/2004 |
| WO | WO-2004/101745 A2 | 11/2004 |
| WO | WO-2005/027727 A2 | 3/2005 |
| WO | WO-2006/002097 A2 | 1/2006 |
| WO | WO-2006/028576 A2 | 3/2006 |
| WO | WO-2007/133702 A2 | 11/2007 |
| WO | WO-2008/137488 A1 | 11/2008 |
| WO | WO-2009/146218 A2 | 12/2009 |
| WO | WO-2010/081488 A1 | 7/2010 |
| WO | WO-2010/141738 A2 | 12/2010 |
| WO | WO-2011/056561 A1 | 5/2011 |
| WO | WO-2011/104671 A1 | 9/2011 |
| WO | WO-2012/125724 A1 | 9/2012 |
| WO | WO-2012/149334 A2 | 11/2012 |
| WO | WO-2012/162698 A1 | 11/2012 |
| WO | WO-2013/185055 A1 | 12/2013 |
| WO | WO-2014/152157 A2 | 9/2014 |
| WO | WO-2015/143190 A1 | 9/2015 |
| WO | WO-2016/011265 A2 | 1/2016 |
| WO | WO-2016/145186 A1 | 9/2016 |

OTHER PUBLICATIONS

"The genomic and transcriptomic architecture of 2,000 breast tumours reveals novel subgroups," available in PMC Dec. 21, 2012, published in final edited form as: Nature 486(7403):346-52 (2012) (15 pages).

Abravaya et al., "Detection of point mutations with a modified ligase chain reaction (Gap-LCR)," Nucleic Acids Res. 23(4):675-82 (1995).

Al-Hajj et al., "Prospective identification of tumorigenic breast cancer cells," Proc Natl Acad Sci U.S.A. 100(7):3983-8 (2003).

Barany, "Genetic disease detection and DNA amplification using cloned thermostable ligase," Proc Natl Acad Sci USA. 88(1):189-193 (1991).

Bild et al., "Oncogenic pathway signatures in human cancers as a guide to targeted therapies," Nature. 439(7074):353-7 (2006).

Carell et al., "A novel procedure for the synthesis of libraries containing small organic molecules," Angew Chem Int Ed Engl. 33(20):2059-2061 (1994).

Cerami et al., "The cBio cancer genomics portal: an open platform for exploring multidimensional cancer genomics data," Cancer Discov. 2(5):401-4 (2012).

Cho et al., "An unnatural biopolymer," Science. 261(5126):1303-1305 (1993).

Cotton et al., "Reactivity of cytosine and thymine in single-base-pair mismatches with hydroxylamine and osmium tetroxide and its application to the study of mutations," Proc Natl Acad Sci U.S.A. 85(12):4397-401 (1988).

Cull et al., "Screening for receptor ligands using large libraries of peptides linked to the C terminus of the lac repressor," Proc Natl Acad Sci U S A. 89(5): 1865-1869 (1992).

Cwirla et al., "Peptides on phage: a vast library of peptides for identifying ligands," Proc Natl Acad Sci U.S.A. 87(16):6378-82 (1990).

Davis et al., "RAC1P29S is a spontaneously activating cancer-associated GTPase," Proc Natl Acad Sci U.S.A. 110(3):912-7 (2013).

DeWitt et al., "'Diversomers': an approach to nonpeptide, nonoligomeric chemical diversity," Proc Natl Acad Sci U S A. 90(15):6909-6913 (1993).

Dontu et al., "In vitro propagation and transcriptional profiling of human mammary stem/progenitor cells," Genes Dev. 17(10):1253-70 (2003).

Elenbaas et al., "Human breast cancer cells generated by oncogenic transformation of primary mammary epithelial cells," Genes Dev. 15(1):50-65 (2001).

Erb et al., "Recursive deconvolution of combinatorial chemical libraries," Proc Natl Acad Sci U S A. 91(24):11422-11426 (1994).

Esnault et al., "Pint modulates the type 1 immune response," PLoS One. 2(2):e226 (2007) (9 pages).

Extended European Search Report for European Patent Application No. 13800857.8, dated Dec. 1, 2015 (7 pages).

Fodor et al., "Multiplexed biochemical assays with biological chips," Nature. 364(6437):555-556 (1993).

Forbes et al., "COSMIC: mining complete cancer genomes in the Catalogue of Somatic Mutations in Cancer," Nucleic Acids Res. 39:D945-50 (2011).

Gallop et al., "Applications of combinatorial technologies to drug discovery. 1. Background and peptide combinatorial libraries," J Med Chem. 37(9):1233-1251 (1994).

Gianni et al., "Inhibition of the peptidyl-prolyl-isomerase Pin1 enhances the responses of acute myeloid leukemia cells to retinoic acid via stabilization of RARalpha and PML-RARalpha," Cancer Res. 69(3):1016-26 (2009).

Gibbs et al., "Detection of single DNA base differences by competitive oligonucleotide priming," Nucleic Acids Res. 17(7):2437-48 (1989).

Ginestier et al., "Distinct and complementary information provided by use of tissue and DNA microarrays in the study of breast tumor markers," Am J Pathol. 161(4):1223-33 (2002).

Guatelli et al., "Isothermal, in vitro amplification of nucleic acids by a multienzyme reaction modeled after retroviral replication," Proc Natl Acad Sci U S A. 87(5):1874-8 (1990).

Houghten et al., "The use of synthetic peptide combinatorial libraries for the identification of bioactive peptides," Biotechniques. 13(3):412-21 (1992).

International Preliminary Report on Patentability for International Application No. PCT/US2015/040771, dated Jan. 17, 2017 (9 pages).

(56) References Cited

OTHER PUBLICATIONS

International Preliminary Report on Patentability for International Patent Application No. PCT/US2013/044747, dated Dec. 9, 2014 (8 pages).
International Preliminary Report on Patentability for International Patent Application No. PCT/US2015/021522, dated Sep. 21, 2016 (8 pages).
International Search Report and Written Opinion for International Application No. PCT/US13/44747, dated Nov. 12, 2013 (18 pages).
International Search Report and Written Opinion for International Application No. PCT/US14/27017, dated Oct. 28, 2014 (19 pages).
International Search Report and Written Opinion for International Application No. PCT/US15/21522, dated Aug. 10, 2015 (19 pages).
International Search Report and Written Opinion for International Application No. PCT/US15/40771, dated Jun. 30, 2016 (13 pages).
International Search Report and Written Opinion for International Application No. PCT/US16/21759, dated Aug. 12, 2016 (18 pages).
International Search Report and Written Opinion for International Application No. PCT/US2012/029077, dated Jul. 18, 2012 (8 pages).
International Search Report for International Application No. PCT/US2012/039850, dated Oct. 3, 2012 (3 pages).
Jeong et al., "Novel role of Pin1 induction in type II collagen-mediated rheumatoid arthritis," J Immunol. 183(10):6689-97 (2009).
Jäger et al., "Sequence determinants of thermodynamic stability in a WW domain—an all-beta-sheet protein," Protein Sci. 18(8):1806-13 (2009).
Kao et al., "Correlation of microarray-based breast cancer molecular subtypes and clinical outcomes: implications for treatment optimization," BMC Cancer. 11:143 (2011) (15 pages).
Keller et al., "Defining the cellular precursors to human breast cancer," Proc Natl Acad Sci U.S.A. 109(8):2772-7 (2012).
Kunju et al., "EZH2 and ALDH-1 mark breast epithelium at risk for breast cancer development," Mod Pathol. 24(6):786-93 (2011).
Kwoh et al., "Transcription-based amplification system and detection of amplified human immunodeficiency virus type 1 with a bead-based sandwich hybridization format," Proc Natl Acad Sci U S A. 86(4):1173-7 (1989).
Lam et al., "A new type of synthetic peptide library for identifying ligand-binding activity," Nature. 354(6348):82-4 (1991).
Lam et al., "Prolyl isomerase Pin1 is highly expressed in Her2-positive breast cancer and regulates erbB2 protein stability," Mol Cancer 7(91):1-12 (2008).
Lam, "Application of combinatorial library methods in cancer research and drug discovery," Anticancer Drug Des. 12(3):145-67 (1997).
Lee et al., "Death-associated protein kinase 1 phosphorylates Pin1 and inhibits its prolyl isomerase activity and cellular function," Mol Cell. 42(2):147-59 (2011).
Linder et al., "Pharmacogenetics: a laboratory tool for optimizing therapeutic efficiency," Clin Chem. 43(2):254-66 (1997).
Liou et al., "Loss of Pin1 function in the mouse causes phenotypes resembling cyclin D1-null phenotypes," Proc Natl Acad Sci U.S.A. 99(3):1335-40 (2002).
Luo et al., "Amplification and overexpression of CTTN (EMS1) contribute to the metastasis of esophageal squamous cell carcinoma by promoting cell migration and anoikis resistance," Cancer Res. 66(24):11690-9 (2006).
Luo et al., "Prolyl isomerase Pin1 acts downstream of miR200c to promote cancer stem-like cell traits in breast cancer," Cancer Res. 74(13):3603-16 (2014).
Ma et al., "A functional polymorphism in PIN1 that prevents its suppression by AP4 is associated with delayed onset of Alzheimer's disease," available in PMC Apr. 1, 2013, published in final edited form as: Neurobiol Aging. 33(4):804-13 (2012) (18 pages).

Madura et al., "N-recognin/Ubc2 interactions in the N-end rule pathway," J Biol Chem. 268(16):12046-54 (1993).
Mani et al., "The epithelial-mesenchymal transition generates cells with properties of stem cells," Cell 133: 704-715 (2008).
Maxam et al., "A new method for sequencing DNA," Proc Natl Acad Sci U.S.A. 74(2):560-4 (1977).
Mori et al., "A dual inhibitor against prolyl isomerase Pin1 and cyclophilin discovered by a novel real-time fluorescence detection method," Biochem Biophys Res Commun. 406(3):439-43 (2011).
Nagaoka et al., "Possible involvement of peptidylprolyl isomerase Pin1 in rheumatoid arthritis," Pathol Int. 61(2):59-66 (2011) (Abstract only).
Nakamura et al., "Proline isomer-specific antibodies reveal the early pathogenic tau conformation in Alzheimer's disease" Cell. 149(1):232-44 (2012).
Nakazawa et al., "UV and skin cancer: specific p53 gene mutation in normal skin as a biologically relevant exposure measurement," Proc Natl Acad Sci U.S.A. 91(1):360-4 (1994).
Office Action for U.S. Appl. No. 14/334,052, dated Nov. 20, 2014 (21 pages).
Orita et al., "Detection of polymorphisms of human DNA by gel electrophoresis as single-strand conformation polymorphisms," Proc Natl Acad Sci U.S.A. 86(8):2766-70 (1989).
Parker et al., "Supervised risk predictor of breast cancer based on intrinsic subtypes," J. Clin. Oncol. 27(8):1160-7 (2009).
Parulekar et al., "A randomized controlled trial to evaluate inhibition of T-cell costimulation in allergen-induced airway inflammation," Am J Respir Crit Care Med. 187(5):494-501 (2013).
Petruk et al., "TrxG and PcG proteins but not methylated histones remain associated with DNA through replication," Cell. 150(5):922-33 (2012).
Ranganathan et al., "Structural and functional analysis of the mitotic rotamase Pin1 suggests substrate recognition is phosphorylation dependent," Cell. 89(6):875-86 (1997).
Ryo et al., "Pin1 regulates turnover and subcellular localization of beta-catenin by inhibiting its interaction with APC," Nat Cell Biol. 3(9):793-801 (2001).
Saiki et al., "Genetic analysis of amplified DNA with immobilized sequence-specific oligonucleotide probes," Proc Natl Acad Sci U.S.A. 86(16):6230-4 (1989).
Sanger et al., "DNA sequencing with chain-terminating inhibitors," Proc Natl Acad Sci U.S.A. 74(12):5463-7 (1977).
Schmidt et al., "The humoral immune system has a key prognostic impact in node-negative breast cancer," Cancer Res. 68(13):5405-13 (2008).
Scott et al. "Searching for peptide ligands with an epitope library," Science. 249(4967):386-90 (1990).
Terzic et al., "Inflammation and colon cancer," Gastroenterology 138(6):2101-14 (2010) (19 pages).
Tun-Kyi et al., "Essential role for the prolyl isomerase Pin1 in Toll-like receptor signaling and type I interferon-mediated immunity," Nat Immunol. 12(8):733-41 (2011) (27 pages).
Written Opinion of the International Searching Authority for International Application No. PCT/US2012/039850, dated Oct. 3, 2012 (5 pages).
Wulf et al., "Pin1 is overexpressed in breast cancer and cooperates with Ras signaling in increasing the transcriptional activity of c-Jun towards cyclin D1," EMBO J. 20(13):3459-72 (2001).
Yu et al. "let-7 regulates self renewal and tumorigenicity of breast cancer cells," Cell. 131(6):1109-23 (2007).
Zhang et al., "Identification of tumor-initiating cells in a p53-null mouse model of breast cancer," Cancer Res. 68(12):4674-82 (2008).
Zuckermann et al., "Discovery of nanomolar ligands for 7-transmembrane G-protein-coupled receptors from a diverse N-(substituted)glycine peptoid library," J Med Chem. 37(17):2678-85 (1994).

* cited by examiner

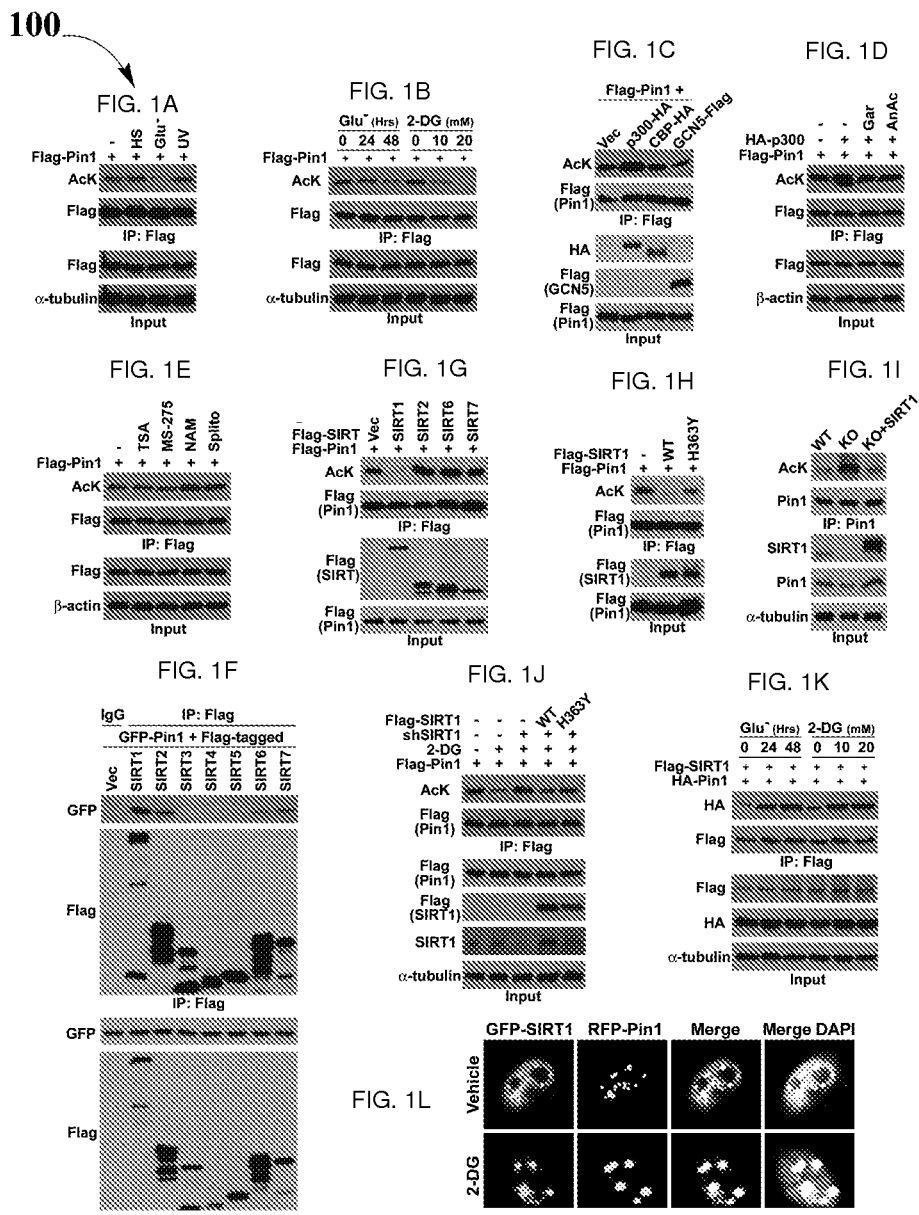

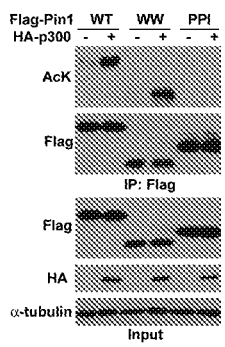
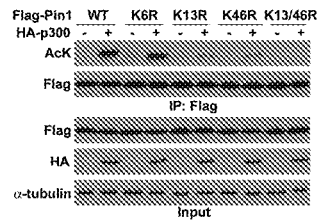
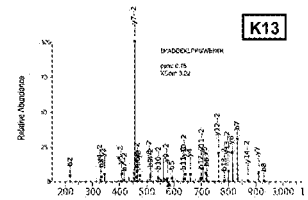
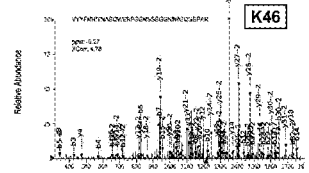
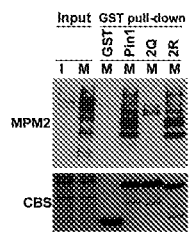
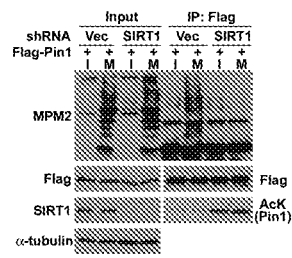
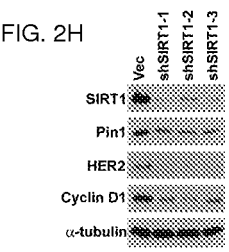
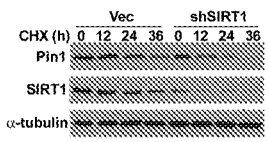
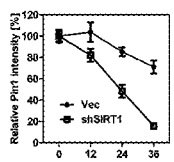
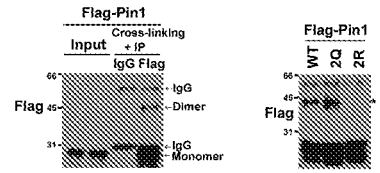
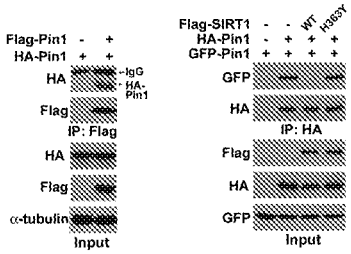
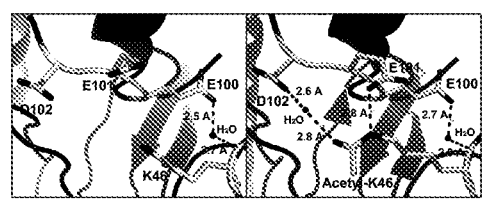
FIG. 2A – FIG. 2O

FIG. 3A
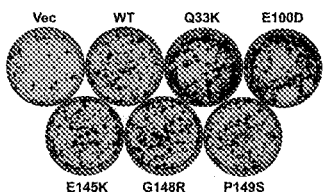
FIG. 3B
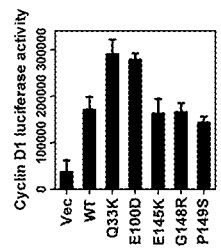
FIG. 3C
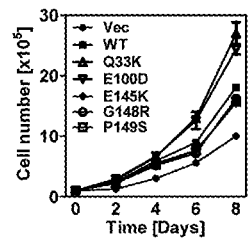
FIG. 3D
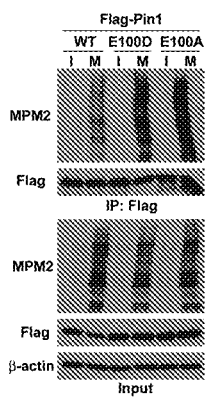
FIG. 3E
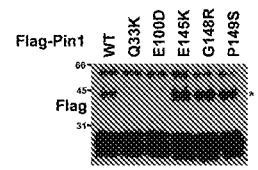
FIG. 3F
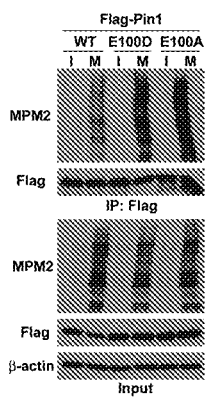
FIG. 3G
FIG. 3H
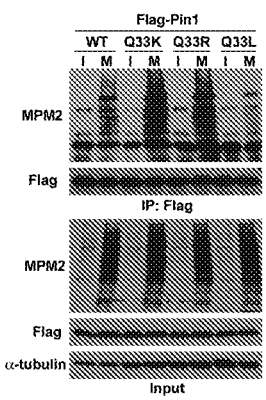
FIG. 3I
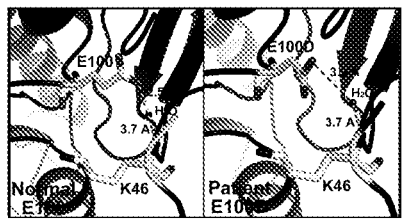
FIG. 3J
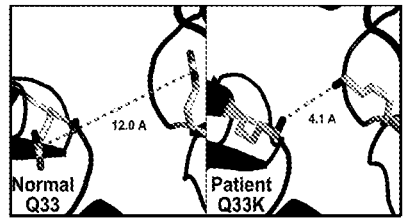

BIOMARKERS FOR PIN1-ASSOCIATED DISORDERS

STATEMENT AS TO FEDERALLY FUNDED RESEARCH

This invention was made with government support under Grant No. DA031663, CA167677, CA122434, AG039405 and HL111430 awarded by the National Institutes of Health. The government has certain rights in the invention.

BACKGROUND

Field of the Disclosure

The present disclosure relates in general to diagnosis and prognosis and, more specifically, to biomarkers and targets for diagnosis, prognosis, and management of Pin1-associated disorders.

BACKGROUND INFORMATION

Pin1 is a highly conserved protein that catalyzes the isomerization of only phosphorylated Ser/Thr-Pro bonds (Ranganathan, et al., 1997; Yaffe, et al., 1997; Shen, et al., 1998; Lu, et al., 1999; Crenshaw, et al., 1998; Lu, et al., 1999; Zhou, et al., 1999). In addition, Pin1 includes an N-terminal WW domain, which functions as a phosphorylated Ser/Thre-Pro binding module PMID: 10037602. The specificity of Pin1 activity is pivotal for cancer cell growth; where depletion or mutations of Pin1 cause growth arrest, affect cell cycle checkpoints and induce premature mitotic entry, mitotic arrest and apoptosis in human tumor cells, yeast or *Xenopus* extracts (Lu, et al., 1996; Winkler, et al., 2000; Hani, et al., 1999). Pin1-catalyzed prolyl isomerization regulates the conformation and function of these phosphoprotein substrates and facilitates dephosphorylation because of the conformational specificity of some phosphatases. Pin1-dependent peptide bond isomerization is a critical post-phosphorylation regulatory mechanism, thus allowing cells to turn phosphoprotein function on or off with high efficiency and specificity during temporally regulated events, including the cell cycle.

However, Pin1 has shown to be aberrant expression in a large number of cell proliferative disorders. A large and increasing body of evidence has shown that Pin1 is a major regulator of oncogenes and tumor suppressors, suggesting that Pin1 inhibitors may have the unique and desired property to inhibit numerous cancer-driving pathways for treating aggressive or drug-resistant cancers (Liou et al., 2011; Lu et al., 2007; Lu et al., 2006).

Pin1 overexpression has been shown to be involved in many human cancers and is correlated with poor prognosis (Ayala et al., 2003; Bao et al., 2004). Pin1 overexpression is prevalent in approximately 60 different human cancer types examined, and the level of Pin1 overexpression is tightly linked to poor clinical outcome of cancer patients. In contrast, the people who carry some genetic variants that reduce Pin1 expression have lower risk for different cancers.

Targeted drugs are often ineffective against aggressive solid tumors largely due to the activation of many cancer-driving pathways. Pin1 activates dozens of cancer-driving molecules, but its activation mechanisms and therapeutic potential in cancer are not clear.

Therefore, Pin1 biomarkers may be useful for detecting the level of monomeric, active Pin1 levels in potential Pin1-associated disorders, thus leading to the identification of appropriate patient groups that have improved probability of responding to Pin1-targeted therapeutic strategies.

SUMMARY OF THE INVENTION

Methods for the use of Pin1 biomarkers for diagnostic applications are disclosed. More particularly, the present disclosure includes methods useful in identifying, stratifying, diagnosing, and monitoring the progression of Pin1-associated disorders through measurements or quantifications of Pin1 genetic mutations and/or protein modifications. Detection of Pin1 biomarkers may indicate abnormal cell growth and the presence of aberrant levels of active Pin1.

In one embodiment, elevated monomeric Pin1 levels may be detected by Pin1 biomarkers, which may include Pin1 Q33K or E100D driver mutations, and deacetylation of Pin1 on Lys13 and Lys46, among others. Pin1 biomarkers may include these genetic mutations and Pin1 modifications along with other previously identified modifications including dephosphorylation of S16, phosphorylation of S65, phosphorylation of S138, dephosphorylation of S71, desumoylation of K6, and desumoylation of K63, promote the monomeric and active form of the Pin1 enzyme.

Another aspect of the disclosure is human cancer-derived Pin1 mutations Q33K or E100D may keep Pin1 in the constitutively active monomer, and enhance Pin1 tumorigenic activity by disrupting Pin1 WW domain-mediated inhibitory dimerization. Pin1 Q33K or E100D may be driver mutations by promoting the active, monomeric form of Pin1 as supported by the Pin1 crystal structure and molecular modeling. Additionally, post-translational protein modifications of Pin1 that may serve as biomarkers for identifying cancers or conditions that may benefit from treatment targeting Pin1 include deacetylation of K13 and K46 that promotes Pin1 active monomer and function, dephosphorylation of S71 that activates Pin1 catalytic activity and function (PMID:21497122), dephosphorylation of S16 that increases Pin1 substrate binding (PMID: 11723108), desumoylation of K6 and K63 that promotes substrate binding and catalytic activity as well as Pin1 oncogenic activity (PMID:23633483), or phosphorylation of S65 that increases Pin1 protein stability (PMID: 16118204), and phosphorylation of S138 that increases Pin1 catalytic activity and nuclear translocation (PMID: 22566623).

Another aspect of the present disclosure provides a method for facilitating the diagnosis of a state associated with abnormal cell growth in a subject by detecting the level of a monomeric Pin1 in a sample from the subject as an indication of whether the subject should be treated with an anti-Pin1 drug. The present disclosure relates to a method including the steps of detecting a level of monomeric Pin1, including deacetylation of K13, deacetylation of K46, dephosphorylation of S16, desumoylation of K6, desumoylation of K63, phosphorylation of S65, phosphorylation of S138, dephosphorylation of S71, in a test sample and comparing the level of monomeric Pin1 in the test sample with the level in a control sample, where a difference in quantity of expression in said test sample compared to the control sample is indicative of a Pin1-associated disorder state.

Another aspect of the present disclosure provides a method for facilitating the diagnosis of a state associated with abnormal cell growth in a subject by detecting the presence of the Pin1 Q33K driver mutation or Pin1 E100D driver mutation in a sample from the subject as an indication of whether the subject should be treated with an anti-Pin1 drug. The present disclosure relates to a method including the steps of detecting a level of monomeric Pin1, including Q33K or E100D, in a test sample and comparing the level of monomeric Pin1 in the test sample with the level in a control sample, where a difference in quantity of expression in said test sample compared to the control sample is indicative of a Pin1-associated disorder state.

In one embodiment, the test sample may be a body fluid sample, such as blood, ascites, urine, or brain fluid, among others. In some embodiments, disclosure relates to tissue test samples, such as breast, uterus, ovarian, brain, endometrium, cervical, colon, esophagus, hepatocellular, kidney, mouth, prostate, liver, lung, skin, or testicular test samples, among others.

In another embodiment, the method includes detecting a level of monomeric Pin1 to stage an abnormal cell growth in order to evaluate the extent of metastasis of abnormal cell growth, such as cancer.

In a further embodiment, the disclosure relates to a kit for determining a stage of abnormal cell growth in a subject including one or more reagents for detecting a level of Pin1 in a test sample obtained from the subject. Specifically encompassed by the present disclosure are kits for staging of abnormal cell growth of various types of cancer.

In another embodiment, Pin1 molecules may be used as biomarkers to predict drug activity in a subject with a Pin1-associated disease. Using the methods described in the present disclosure, the presence, absence and/or quantity of the monomeric Pin1 levels may be detected, and may be correlated with one or more biological states in vivo, which may be used to determine whether a Pin1 inhibitor may be administered to a subject or to assess whether a disease may respond to favorably to a Pin1 inhibitor. Therefore, the disclosure includes evaluating the potential efficacy of a treatment of a Pin1-associated disease by monitoring the levels of monomeric Pin1.

In another embodiment, Pin1 molecules may be used to monitor the efficacy of a drug regiment in a subject with a Pin1-associated disease. Using the methods described in the present disclosure, the presence, absence and/or quantity of the monomeric Pin1 levels may be detected, and may be correlated with one or more biological states in vivo, which may be used to determine whether a Pin1 inhibitor may be efficacious in modifying the levels of monomeric Pin1 in the subject. Therefore, the disclosure includes evaluating the efficacy of a treatment of a Pin1-associated disease by monitoring the levels of monomeric Pin1.

In another embodiment, Pin1 driver mutations may be used as biomarkers to predict drug activity, or as biomarkers of the pharmacogenomic profile of a subject. Using the methods described in the present disclosure, the presence of the Pin1 driver mutations Q33K or E100D may be detected, and may be correlated with one or more biological states in vivo, which may be used to determine whether a Pin1 inhibitor may be administered to a subject or to assess whether a cancer type will respond to more favorably to a Pin1 inhibitor. Therefore, the disclosure includes evaluating the efficacy of a treatment of an abnormal cell growth by monitoring the levels of monomeric Pin1.

In an embodiment, the present disclosure includes determining the presence of the Pin1 driver mutations Q33K or E100D by nucleic acid sequencing techniques. Samples for nucleic acid sequencing may be obtained by tissue samples from the subject.

In an embodiment, the present disclosure includes determining monomeric Pin1 level by utilizing an antibody. Antibody fragments may be obtained using conventional techniques well-known to those with skill in the art, and the fragments are screened for utility in the same manner as are intact antibodies.

In the diagnostic assays of the disclosure, the antibody may be a polyclonal antibody or a monoclonal antibody and in a preferred embodiment is a labeled antibody.

A further aspect of the disclosure is the identification of the mechanism for cancer-derived Pin1 mutations Q33K or E100D, or SIRT1-mediated deacetylation of K13 and K46, which may keep Pin1 in the constitutively active monomer and enhance Pin1 tumorigenic activity by disrupting WW domain-mediated inhibitory dimerization, which is supported by the crystal structure of Pin1 dimer (Ranganathan et al., 1997) and molecular modeling.

Detecting these said Pin1 biomarkers may provide opportunity to identify individuals with Pin1-associated disorder and monitor treatment response.

In a first aspect, the invention features a method of treating a proliferative or immune disorder in a subject. The method involves obtaining a sample from the subject; determining whether an aberrant mutation is present in the gene encoding Pin1 in the sample; and treating the subject with a retinoic acid compound if at least one of the aberrant mutations is present; in which the aberrant mutation encodes an amino acid substitution in Pin1 selected from: Q33K or E100D.

In a second aspect, the invention features a method of diagnosing a subject as having a proliferative or immune disorder, or a propensity to develop a proliferative or immune disorder. The method involves obtaining a sample from the subject and determining whether an aberrant mutation is present in the gene encoding Pin1 in the sample, in which the aberrant mutation encodes an amino acid substitution in Pin1 selected from Q33K or E100D, and the presence of the aberrant mutation is indicative of a subject having a proliferative or immune disorder, or a propensity to develop a proliferative or immune disorder.

In some embodiments of the above aspects, the step of determining whether an aberrant mutation is present includes sequencing all or a portion of the Pin1 gene.

In other embodiments, the step of determining whether an aberrant mutation is present includes contacting the sample with a nucleic acid probe specific for Pin1. In certain embodiments, the probe is bound to a microarray.

In some embodiments, the method further involves determining whether an aberrant post-translational modification of Pin1 is present and treating the subject with a retinoic acid compound if at least one of the aberrant post-translational modifications is present, in which the post-translational modification is selected from the group consisting of deacetylation of K13, deacetylation of K46, dephosphorylation of S16, desumoylation of K6, desumoylation of K63, phosphorylation of S65, phosphorylation of S138, and dephosphorylation of S71.

In certain embodiments, the method further involves determining whether an aberrant post-translational modification of Pin1 is present, in which the post-translational modification is selected from the group consisting of deacetylation of K13, deacetylation of K46, dephosphorylation of S16, desumoylation of K6, desumoylation of K63, phosphorylation of S65, phosphorylation of S138, and dephosphorylation of S71, and in which the presence of an aberrant post-translational modification of Pin1 is a further indication of a subject having a proliferative or immune disorder, or a propensity to develop a proliferative or immune disorder.

In particular embodiments, the aberrant post-translational modification is selected from the group consisting of desumoylated K6 and desumoylated K63. In specific embodiments, the step of determining whether an aberrant post-translational modification is present includes contacting the sample with a binding moiety specific for desumoylated Pin1. In alternate embodiments, the step of determining whether an aberrant post-translational modification is present includes isolating Pin1 protein from the sample and contacting the isolated Pin1 with a binding moiety specific for desumoylated Pin1 or desumoylated lysine.

In certain embodiments, the aberrant post-translational modification is selected from the group consisting of dephosphorylated S16 and/or dephosphorylated S71.

In particular embodiments, the step of determining whether an aberrant post-translational modification is present includes contacting the sample with a binding moiety specific for dephosphorylated Pin1. In other embodiments, the step of determining whether an aberrant post-translational modification is present includes isolating Pin1 protein from the sample and contacting the isolated Pin1 with a binding moiety specific for dephosphorylated Pin1 or dephosphorylated serine.

In certain embodiments, the aberrant post-translational modification is selected from the group consisting of deacetylated K13 and deacetylated K46.

In particular embodiments, the step of determining whether an aberrant post-translational modification is present includes contacting the sample with a binding moiety specific for deacetylated Pin1. In other embodiments, the step of determining whether an aberrant post-translational modification is present includes isolating Pin1 protein from the sample and contacting the isolated Pin1 with a binding moiety specific for deacetylated Pin1 or deacetylated lysine.

In certain embodiments, the aberrant post-translational modification is phosphorylated S138.

In particular embodiments, the step of determining whether an aberrant post-translational modification is present includes contacting the sample with a binding moiety specific for phosphorylated Pin1. In other embodiments, the step of determining whether an aberrant post-translational modification is present includes isolating Pin1 protein from the sample and contacting the isolated Pin1 with a binding moiety specific for phosphorylated Pin1 or phosphorylated serine.

In another aspect, the invention features a method of treating a proliferative or immune disorder in a subject. The method involves obtaining a sample from the subject; determining whether an aberrant post-translational modification of Pin1 is present; and treating the subject with a retinoic acid compound if at least one of the aberrant post-translational modifications is present; in which the post-translational modification is selected from deacetylation of K13 and deacetylation of K46.

In a further aspect, the invention features a method of diagnosing a subject as having a proliferative or immune disorder, or a propensity to develop a proliferative or immune disorder. The method involves obtaining a sample from the subject and determining whether an aberrant post-translational modification of Pin1 is present, in which the post-translational modification is selected from deacetylation of K13 and deacetylation of K46, and the presence of an aberrant post-translational modification of Pin1 is indicative of a subject having a proliferative or immune disorder, or a propensity to develop a proliferative or immune disorder.

In some embodiments, the step of determining whether an aberrant post-translational modification is present includes contacting the sample with a binding moiety specific for deacetylated Pin1.

In other embodiments, the step of determining whether an aberrant post-translational modification is present includes isolating Pin1 protein from the sample and contacting the isolated Pin1 with a binding moiety specific for deacetylated Pin1 or deacetylated lysine.

In some embodiments, the method further involves determining whether a further aberrant post-translational modification of Pin1 is present and treating the subject with a retinoic acid compound if at least one of the further aberrant post-translational modification is present, in which the post-translational modification is selected from the group consisting of dephosphorylation of S16, desumoylation of K6, desumoylation of K63, phosphorylation of S65, phosphorylation of S138, and dephosphorylation of S71.

In some embodiments, the method further involves determining whether a further aberrant post-translational modification of Pin1 is present, in which the post-translational modification is selected from the group consisting of dephosphorylation of S16, desumoylation of K6, desumoylation of K63, phosphorylation of S65, phosphorylation of S138, and dephosphorylation of S71, and in which the presence of an aberrant post-translational modification of Pin1 is a further indication of a subject having a proliferative or immune disorder, or a propensity to develop a proliferative or immune disorder.

In certain embodiments, the further aberrant post-translational modification is selected from the group consisting of desumoylated K6 and desumoylated K63.

In particular embodiments, the step of determining whether an aberrant post-translational modification is present includes contacting the sample with a binding moiety specific for desumoylated Pin1. In other embodiments, the step of determining whether an aberrant post-translational modification is present includes isolating Pin1 protein from the sample and contacting the isolated Pin1 with a binding moiety specific for desumoylated Pin1 or desumoylated lysine.

In certain embodiments, the further aberrant post-translational modification is selected from the group consisting of dephosphorylated S16 and dephosphorylated S71.

In particular embodiments, the step of determining whether an aberrant post-translational modification is present includes contacting the sample with a binding moiety specific for dephosphorylated Pin1. In other embodiments, the step of determining whether an aberrant post-translational modification is present includes isolating Pin1 protein from the sample and contacting the isolated Pin1 with a binding moiety specific for dephosphorylated Pin1 or dephosphorylated serine.

In certain embodiments, the further aberrant post-translational modification is phosphorylated S138.

In particular embodiments, the step of determining whether an aberrant post-translational modification is present includes contacting the sample with a binding moiety specific for phosphorylated Pin1. In other embodiments, the step of determining whether an aberrant post-translational modification is present includes isolating Pin1 protein from the sample and contacting the isolated Pin1 with a binding moiety specific for phosphorylated Pin1 or phosphorylated serine.

In embodiments of any of the above aspects, the disorder is a proliferative disorder.

In some embodiments, the proliferative disorder is selected from the group consisting of breast cancer, colon cancer, and prostate cancer. In certain embodiments, the proliferative disorder is metastatic cancer. In particular embodiments, proliferative disorder is a drug-resistant cancer.

In embodiments of any of the above aspects, the disorder is an immune disorder.

In certain embodiments, the immune disorder is an autoimmune disorder. In other embodiments, the immune disorder is selected from the group consisting of asthma and lupus.

In some embodiments of any of the above aspects, the retinoic acid compound is part of a pharmaceutical composition formulated for long-term delivery of the retinoic acid compound after injection of the composition into the subject.

In certain embodiments, the composition is formulated as an injectable depot system, an injectable drug suspension, an injectable microsphere, or an injectable gel. In particular embodiments, the injectable drug suspension is an oil-based suspension.

In various embodiments, the composition is formulated for intravenous injection or intramuscular injection. In particular embodiments, the composition is formulated as an injectable gel and for intramuscular injection. In a specific embodiment, the injectable gel remains in the muscle for at least 4-6 weeks after injection.

In some embodiments, the composition is formulated to delay the metabolism of the retinoic acid compound.

In certain embodiments, the composition includes one or more liposomes including the retinoic acid compound.

In some embodiments, the composition further includes a pharmaceutically acceptable excipient.

In various embodiments, the retinoic acid compound is all-trans retinoic acid (ATRA).

Numerous other aspects, features and benefits of the present disclosure may be made apparent from the following detailed description taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

FIG. 1 depicts HTS results for glucose starvation induced Pin1 deacetylation in cells.

(A) Different stress tests for inducing Pin1 deacetylation in cells (Glu-, glucose starvation; HS, heat shock; UV, UV radiation).

(B) Mimic glucose starvation with 2-deoxyglucose (2-DG) increased Pin1 deacetylation along with Glu-dose-dependently.

(C) Overexpression of p300-HA increased Pin1 acetylation in cells. Various histone acetyl transferases were co-transfected with Flag-Pin1 into cells, followed by assaying acetylated Pin1.

(D) p300 inhibitors, Garcinol (Gar) and Anacardic acid (AnAc), reversed p300-increased Pin1 acetylation.

(E) Class III HDAC inhibitors, Nicotinamide (NAM) and Splitomicin (Splito), increased Pin1 acetylation in cells.

(F) GFP-Pin1 was co-IPed with SIRT1, SIRT2, SIRT6, and SIRT7.

(G) SIRT1 overexpression selectively induced Pin1 deacetylation in cells. Flag-SIRT1, 2, 6, 7 were co-transfected with Pin1 into cells, followed by assaying acetylated Pin1.

(H) Wild type (WT) SIRT1, but not its inactive H363Y mutant induced Pin1 deacetylation.

(I) SIRT1 KO MEFs exhibiting high Pin1 acetylation, which was rescued by re-constitution of WT-SIRT1.

(J) 2-DG-mediated Pin1 deacetylation was attenuated by SIRT1 KD, which was recovered by overexpression of WT SIRT1, but not its inactive mutant in cells.

(K) Glu⁻ and 2-DG increased Pin1 and SIRT1 interaction, as shown by co-IP.

(L) 2-DG increased Pin1 and SIRT1 interaction, as shown by double immunostaining, followed by fluorescence confocal microscopy.

FIG. 2 depicts the effect of deacetylation at K13 and K46 residues in Pin1 activity.

(A) p300 acetylated Pin1 in the N-terminal WW domain in cells. Cells were co-transfected with HA-p300 and Flag-Pin1 (WT), or its WW or PPI domain, followed by assaying acetylated Pin1.

(B) p300 acetylated Pin1 at K13 and K46 residues in the WW domain.

(C) K13 and K46 residues in Pin1 are evolutionally conserved.

(D and E) LC/Mass spectrum analysis revealing Pin1 acetylation at K13 (D) and K46 (E). Cells were transfected with HA-Pin1 and Myc-p300 and then treated with TSA and NAM, followed by IP with anti-HA before SDS-PAGE and then mass spectrum analysis.

(F) GST-K13/46Q (GST-2Q), an acetylation-mimicking mutant, exhibiting reduced Pin1 activity in substrate binding, as assayed by reduced MPM2 signals pulled down by GST-2Q, compared to those by WT-GST-Pin1. GST-2R, GST-K13/46R; CBS, Commassie blue staining.

(G) KD of SIRT1 reducing Pin1 substrate-binding activity. Cells expressing Flag-Pin1 were infected with shSIRT1 and arrested in interphase (I) or mitosis (M) to induce MPM2 antigens, followed by assaying Pin1 binding to MPM2 epitope by Co-IP.

(H) Stable KD of SIRT1 decreased protein levels of Pin1 and its downstream targets, cyclin D1 and HER2 in cells.

(I and J) SIRT1 KD significantly reducing Pin1 protein half-life from over 36 h to 24 h using the cyclohexamide (CHX) chase (I), with quantification data being presented in (J) (n=3).

(K) Pin1 as dimer in cells, as shown by co-IP of HA-Pin1 and Flag-Pin1.

(L) WT SIRT1, but not its inactive H363Y mutant disrupted Pin1 dimerization, as shown by co-IP of GFP-Pin1 and HA-Pin1.

(M) Detection of Flag-Pin1 dimer in cells as detected by crosslinking with EGS. Flag-Pin1-expressing cells were crosslinked with EGS, and IPed with control IgG or Flag agarose followed by immunoblotting with Flag antibody.

(N) Acetylation-mimicking Flag-2Q Pin1 demonstrating more dimer formation, whereas acetylation-resistant Flag-2R less dimer formation than WT Flag-Pin1. Asterisk, Pin1 dimer.

(O) Structural basis of Pin1 acetylation favoring dimers. Molecular modeling analysis revealing that although there are two water-mediated hydrogen bonds between K46 back bone and E100 in native Pin1 (left panel), K46 acetylation formed additional hydrogen bonds between the K46 side chain with the backbone and side chain of E101 and D102 (right panel).

FIG. 3 shows that cancer-derived Q33K and E100D mutations behave monomeric and tumorigenic.

(A) Summary of human Pin1 missense mutations from the cBio Cancer Genomics Portal and the COSMIC database.

(B) Q33K and E100D mutations increasing Pin1 activity, as assayed by activating the cyclin D1 promoter (C) Q33K and E100D mutations increased Pin1 oncogenic activity, as assayed by enhancing cell growth.

(D) Q33K and E100D mutations increased Pin1 oncogenic activity, as assayed by enhancing foci formation.

(E) Q33K and E100D mutations prevented Pin1 dimer formation, as detected by crosslinking with EGS. Asterisk, Pin1 dimer (F) E100A or E100D mutation increased Pin1 substrate binding to MPM2 epitopes, as assaying by Co-IP.

(G) Compared to WT Pin1, Q33R and E100A generated more foci formation as Q33K and E100D did, respectively.

(H) Q33R or Q33K, but not Q33L, mutation increased Pin1 substrate binding to MPM2 epitopes.

(I) The E100D mutation favors Pin1 monomer likely because the hydrogen bonds between E100D and K46 have longer distances than that between E100 and K46 in the WT dimer.

(J) The Q33K mutation favors Pin1 monomer likely because the distance between two Q33K is much shorter than that between two Q33 in the WT dimer so that they repel each other.

DETAILED DESCRIPTION

The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

Definitions

As used here, the following terms may have the following definitions:

"Abnormal cell growth" refers to cell growth which is undesirable or inappropriate (e.g., unregulated cell proliferation or undesirably rapid cell proliferation). Abnormal cell growth can be benign or malignant.

"Activity" refers to a measurable amount of a specific function or role performed by a biological entity in a biophysical process, biochemical reaction, or biochemical process.

"Dimer" refers to a chemical entity including two structurally similar monomers joined by bonds that can be either strong or weak, covalent or intermolecular.

"Elevated levels of a Pin1 biomarker" refers to a level of Pin1 biomarker that is altered thereby indicating elevated Pin1 activity. Elevated levels of a Pin1 biomarker include levels at least 5%, 6%, 7%, 8%, 9%, 10%, 15%, 20%, 25%, 30%, 40%, 50%, 60%, 70%, 80%, 90%, 100%, 200%, 500%, 1000%, or greater than, or 5%, 6%, 7%, 8%, 9%, 10%, 15%, 20%, 25%, 30%, 40%, 50%, 60%, 70%, 80%, 90%, 100% less than the biomarker levels measured in a normal, disease fee subject or tissue.

"Driver mutations" refers to changes of the nucleotide sequence or sequences in genes that confer growth advantages on the cells that carry them. Generally, the cells harboring the driver mutation are positively selected during the evolution of cancer.

"Pin1" refers to peptidyl-prolyl cis/trans isomerase (PPlase) that isomerizes phospho-Serine/Threonine-Proline motifs.

"Pin1-associated disorder" refers to a disorder or a state (e.g., a disease state) which is associated with abnormal cell growth or aberrant levels of Pin1 biomarker. Pin1-associated disorders include cancers, malignancies, tumors, and proliferative or inflammatory arthritic conditions.

"Pin1 biomarker" refers to an objective biochemical marker capable of being indicative of Pin1 activity levels in an organism or a sample. Pin1 biomarkers may include nucleic acid molecules (e.g., mRNA, DNA), a peptide sequences (e.g., amino acid sequences), nucleic acid sequences which are homologous to Pin1 gene sequences, peptide sequences which are homologous to Pin1 peptide sequences, antibodies to Pin1 protein, substrates of Pin1 protein, binding partners of Pin1 protein, and quaternary structure of Pin1.

"Pin1 mutations" refers to a change of the nucleotide sequence of wild type Pin1. Pin1 mutations may be the result from heredity, unrepaired damage to DNA or to RNA genomes, errors in the process of replication, or from the insertion or deletion of segments of DNA by mobile genetic elements.

"Subject" refers to living organisms, e.g., prokaryotes and eukaryotes. Examples of subjects include mammals, e.g., humans, dogs, cows, horses, kangaroos, pigs, sheep, goats, cats, mice, rabbits, rats, and transgenic non-human animals.

"Substrate" refers to a molecule upon which an enzyme acts.

"Test sample" refers to samples obtained from a subject which can be used within the methods described herein. Typical samples from a subject include tissue samples, fluid samples, tumor samples, blood, urine, biopsies, lymph, saliva, phlegm, and pus, among others.

DESCRIPTION OF THE INVENTION

The present disclosure describes biomarkers and targets for diagnosis of Pin1-associated diseases. Methods for diagnosis and prognosis may include detecting the presence or measuring levels of Pin1 biomarkers, such as proteins, nucleic acids, genes, mutations, and antibodies, among others, in the context of a biological sample (e.g., tissue and fluid samples, blood, urine, biopsies, lymph, saliva, phlegm, and pus) in order to determine whether a subject is a candidate for treatment with an Pin1 inhibitor or whether the subject is responsive to a Pin1 inhibitor. Other aspects of the present disclosure is the identification of the mechanism for cancer-derived Pin1 driver mutations, Q33K or E100D, or SIRT1-mediated deacetylation of K13 and K46, which may promote the active form of Pin1 and promote the constitutively active monomeric form. Driver mutations Q33K or E100D and deacetylated K13 or K46 enhance Pin1 tumorigenic activity by disrupting WW domain-mediated inhibitory dimerization, which is supported by the crystal structure of Pin1 dimer (Ranganathan, et al., 1997) and molecular modeling.

PIN1

Pin1 prolyl isomerase promotes tumorigenesis by activating numerous cancer-driving molecules. However, Pin1 activation mechanisms or its therapeutic potential in cancers are unclear.

A common and central signaling mechanism in cell proliferation and transformation is Proline (Pro)-directed Ser/Thr phosphorylation (pSer/Thr-Pro), which has been reported to be modulated by a large number of Pro-directed kinases and phosphatases. In fact, numerous oncogenes and tumor suppressors themselves are directly regulated by Pro-directed phosphorylation and/or can trigger signaling pathways involving Pro-directed phosphorylation. Because several studies have demonstrated that the same kinases often phosphorylate both oncogenes and tumor suppressors, it was not clear how these phosphorylation events are coordinated to promote tumorigenesis until recently.

Further research demonstrated that phosphorylation on serine/threonine-proline motifs of Pin1 substrates creates a binding site for Pin1 binding and subsequent cis/trans prolyl isomerization. Both structural and functional analyses have indicated that Pin1 includes a phosphoserine/threonine-binding module that binds phosphoproteins, and a catalytic activity that specifically isomerizes the phosphorylated phosphoserinelthreonine-proline. Pin1 binds and regulates the activity of a defined subset of phosphoproteins, as well as participating in the timing of mitotic progression. It has also been demonstrated that phosphorylation on Ser/Thr residues immediately preceding Proline on substrates creates a binding site for the WW domain of Pin1. The WW domain acts as phosphoserine-binding module targeting Pin1 to a highly conserved subset of phosphoproteins. Furthermore, the specificity for the phosphorylated Ser/Thr-Pro bond by Pin1 is the only known phosphorylation-dependent PPlase.

Proline uniquely adopts cis and trans conformations, providing a backbone switch by prolyl cis-trans isomerization catalyzed by peptidyl-prolyl cis-trans isomerases (PPlases). A major advance in appreciating the importance of conformational changes after Pro-directed phosphorylation was the identification of the unique PPlase Pin1. Using its protein-targeting WW domain, Pin1 binds to specific pSer/Thr-Pro motif(s) that target Pin1 close to its substrates, where its PPlase domain catalyzes cis-trans isomerization of the pSer/Thr-Pro motifs, which cannot be effectively catalyzed by other known PPlases. Increasing evidence has supported a pivotal role for Pin1 in tumorigenesis.

Pin1 has been shown to be regulated by multiple mechanisms, including transcriptional activation by E2F, inhibition by DAPK1 phosphorylation, activation by PLK or MLK3 phosphorylation, activation by SIRT1 deacetylation, inactivation by p300 acetylation, and/or activation by SENP1 desumoylation. Pin1 overexpression is prevalent in approximately 60 different human cancer types and high Pin1 levels have been shown to correlate with poor clinical outcome in prostate, lung, esophageal, and breast cancers. In contrast, the Pin1 polymorphisms that reduce Pin1 expression are associated with lower risk for multiple cancers in humans, including breast cancer. Moreover, Pin1 knockout (−/−, KO) in mice are resistant to cancer development even when induced by oncogenes such as MMTV-Ras or -HER2.

Conversely, Pin1 overexpression results in centrosome amplification, chromosome instability, and cancer development in vitro and in vivo. Numerous studies have shown that Pin1 activates at least 25 oncogenes/growth enhancers, including PML-RARα, c-Jun, b-catenin, cyclin D1, NF-kB/p65, Raf-1, c-fos, AIB1, Hbx, Stat3, HER2/Neu, Mcl-1, Notch, Akt, c-Rel, v-Rel and Tax, ERa, SF-1, mutant p53, PTP-PEST, PKM2 and c-Myc. Pin1 also inactivates at least 19 tumor suppressors/growth inhibitors, including SMRT, PML, FOXOs, RARa, Smad, TRF1, Fbw7, Rb, AMPK and RUNX3. Thus, Pin1 may amplify oncogenic pathways in the positive and negative feedback mechanisms to turn on numerous oncogenes and/or turn off many tumor suppressors at the same time. This suggests that small molecule inhibitors selectively against Pin1 in cancer cells might have a unique and desirable property to block numerous cancer-driving pathways at the same time.

Pin1 is highly conserved and includes a protein-interacting module, called WW domain, and a catalytically active peptidyl-prolyl isomerase (PPlase). Pin1 is structurally and functionally distinct from members of two other well-characterized families of PPlases, the cyclophilins and the FKBPs. PPlases are ubiquitous enzymes that catalyze the relatively slow prolyl isomerization of proteins, thus allowing relaxation of local energetically unfavorable conformational states.

One aspect of the present disclosure is the identification that cancer-derived genetic mutations or SIRT1-mediated deacetylation keep Pin1 in a constitutively active monomer by disrupting WW domain-mediated inhibitory dimerization. Acetylation occurs in the N-terminal WW domain that contains three lysine residues, K6, K13 and K46. Mutation of K13 or K46, but not K6, partially reduced Pin1 acetylation, while double mutation K13/46R completely abolished Pin1 acetylation, indicating that acetylation likely occurs of K13 and K46, two highly evolutional conserved Lys residues. Importantly, acetylation of K13 and K46 is further confirmed by immunoprecipitating Pin1 from cells, followed by Mass Spec analysis. Thus, cancer-derived genetic mutations or SIRT1-mediated deacetylation keep Pin1 in a constitutively active monomer by disrupting WW domain-mediated inhibitory dimerization.

Additionally, cancer-derived Pin1 mutations, Q33K and E100D Pin1 mutants are more active than WT protein in activating the cyclin D1 promoter and in binding to the Pin1 substrate MPM2 antigens, indicators for Pin1 in vivo activity. Both Q33K and E100D kept Pin1 in a constitutively monomeric form. Q33K or E100D or SIRT1-mediated deacetylation of K13 and K36 disrupt Pin1 dimerization, leading to a constitutively active Pin1 monomer with enhanced tumorigenic activity. Furthermore, Pin1 is activated by S71 dephosphorylation in cancers.

Pin1 Biomarkers

In various embodiments, activation mutation Q33K, activation mutation E100D, deacetylation on K13, deacetylation of K46, or dephosphorylation of Ser71 of Pin1 may be considered Pin1 biomarkers and may be utilized in the diagnosis and prognosis of Pin1-associated diseases. In other embodiments, Pin1 biomarkers may also include Pin1 protein or transcript overexpression, deacetylation of K13, deacetylation of K46, dephosphorylation of S16, phosphorylation of S65, dephosphorylation of S71, phosphorylation of S138, desumoylation on K6, and desumoylation of K63, among others.

In some embodiments, a kit for determining a stage of abnormal cell growth in a subject including one or more reagents for detecting a level of Pin1 in a test sample obtained from the subject may be employed. Specifically encompassed by the present disclosure are kits for staging of abnormal cell growth of various types of cancer.

In other embodiments, Pin1 driver mutations may be used as biomarkers of drug activity, or as biomarkers of the pharmacogenomic profile of a subject. Using the methods described in the present disclosure, the presence of the Pin1 driver mutations Q33K or E100D may be detected, and may be correlated with one or more biological states in vivo, which may be used to determine whether a Pin1 inhibitor may be administered to a subject or to assess whether a cancer type will respond to more favorably to a Pin1 inhibitor. Therefore, the disclosure includes evaluating the efficacy of a treatment of an abnormal cell growth by monitoring the levels of monomeric Pin1.

In one embodiment, the Pin1 dimer crystal structure and a molecular modeling reveal the structural basis for how Pin1 mutations or deacetylation of K13 and K36 disrupt WW domain-mediated inhibitory dimerization. Cancer-derived Pin1 mutations, Q33K or E100D or SIRT1-mediated deacetylation of K13 and K36 disrupt Pin1 dimerization, leading to a constitutively active Pin1 monomer with enhanced tumorigenic activity.

In other embodiments, screening subjects for Pin1 biomarkers may help identify and stratify patients more likely to benefit from treatment with Pin1 inhibitors. Such Pin1 inhibitors may have a significant impact on treating Pin1-associated diseases, such as aggressive and drug-resistant cancers that have developed the ability to simultaneously block numerous cancer-driving pathways. Moreover, Pin1 inhibitors may not ablate Pin1 in normal cells.

Pin1 Biomarkers Identification

Different techniques have enabled measurement of the expression of proteins, or the presence of protein modifications and nucleic acid mutations. Those with skill in the art may use techniques coupled with improved bioinformatics tools to determine with the significance and direct relevance to Pin1 activity or protein levels.

Several techniques, such as, serial analysis of gene expression (SAGE), GeneChip® (Affymetrix, USA) and ONCOMINE, two-dimensional polyacrylamide gel electrophoresis (2D-PAGE) coupled with mass spectrometry had been the primary proteomic technology used. Also, improved tissue-capturing techniques such as laser capture microdissection may improve the specificity of 2D-PAGE. In addition, matrix-assisted laser desorption ionization time-of-flight (MALDI-TOF) mass spectrometry and tandem mass spectrometry may be coupled with 2D electrophoresis.

Other techniques used in antibody-based assays may include immunohistochemistry (IHC) and enzyme-linked immunosorbent assay (ELISA).

In some embodiments, Pin1 biomarkers may be employed in the diagnosis and/or prognosis of a proliferative disorder characterized by overexpression of Pin1 or Pin1 biomarker levels (e.g., reduced Ser71 phosphorylation) in a subject. Proliferative disorders may include, but not be limited to, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, polycythemia vera, lymphoma (Hodgkin's disease, non-Hodgkin's disease), fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, waldenstrom's macroglobulinemia, heavy chain disease, and solid tumors such as sarcomas and carcinomas (e.g., fibrosarcoma, myxosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma), among others.

In further embodiments, Pin1 biomarkers may be employed in the diagnosis and/or prognosis of immune disorders in a subject, e.g., a human subject. The immune disorder may include acne vulgaris, acute respiratory distress syndrome, Addison's disease, adrenocortical insufficiency adrenogenital ayndrome, allergic conjunctivitis, allergic rhinitis, allergic intraocular inflammatory diseases, ANC A-associated small-vessel vasculitis, angioedema, ankylosing spondylitis, aphthous stomatitis, arthritis, asthma, atherosclerosis, atopic dermatitis, autoimmune disease, autoimmune hemolytic anemia, autoimmune hepatitis, Behcet's disease, Bell's palsy, berylliosis, bronchial asthma, bullous herpetiformis dermatitis, bullous pemphigoid, carditis, celiac disease, cerebral ischaemia, chronic obstructive pulmonary disease, cirrhosis, Cogan's syndrome, contact dermatitis, COPD, Crohn's disease, Cushing's syndrome, dermatomyositis, diabetes mellitus, discoid lupus erythematosus, eosinophilic fasciitis, epicondylitis, erythema nodosum, exfoliative dermatitis, fibromyalgia, focal glomerulosclerosis, giant cell arteritis, gout, gouty arthritis, graft-versus-host disease, hand eczema, Henoch-Schonlein purpura, herpes gestationis, hirsutism, hypersensitivity drug reactions, idiopathic cerato-scleritis, idiopathic pulmonary fibrosis, idiopathic thrombocytopenic purpura, inflammatory bowel or gastrointestinal disorders, inflammatory dermatoses, juvenile rheumatoid arthritis, laryngeal edema, lichen planus, Loeffler's syndrome, lupus nephritis, lupus vulgaris, lymphomatous tracheobronchitis, macular edema, multiple sclerosis, musculoskeletal and connective tissue disorder, myasthenia gravis, myositis, obstructive pulmonary disease, ocular inflammation, organ transplant rejection, osteoarthritis, pancreatitis, pemphigoid gestationis, pemphigus vulgaris, polyarteritis *nodosa*, polymyalgia rheumatica, primary adrenocortical insufficiency, primary billiary cirrhosis, pruritis scroti, pruritis/inflammation, psoriasis, psoriatic arthritis, Reiter's disease, relapsing polychondritis, rheumatic carditis, rheumatic fever, rheumatoid arthritis, rosacea caused by sarcoidosis, rosacea caused by scleroderma, rosacea caused by Sweet's syndrome, rosacea caused by systemic lupus erythematosus, rosacea caused by urticaria, rosacea caused by zoster-associated pain, sarcoidosis, scleroderma, segmental glomerulosclerosis, septic shock syndrome, serum sickness, shoulder tendinitis or bursitis, Sjogren's syndrome, Still's disease, stroke-induced brain cell death, Sweet's disease, systemic dermatomyositis, systemic lupus erythematosus, systemic sclerosis, Takayasu's arteritis, temporal arteritis, thyroiditis, toxic epidermal necrolysis, tuberculosis, type-1 diabetes, ulcerative colitis, uveitis, vasculitis, and Wegener's granulomatosis, among others. In further embodiments, Pin1 biomarkers may be employed in the diagnosis and/or prognosis of cocaine addiction.

Diagnostic Assays

Pin1 may be overexpressed in a variety of proliferative disorders, including, but not limited to cancers of the breast, uterus, ovarian, brain, endometrium, cervical, colon, esophagus, hepatocellular, kidney, mouth, prostate, liver, lung, skin, endocrine and testicular and its levels are correlated with the nuclear grade of tumors, as described above.

One aspect of the disclosure pertains to monitoring the effectiveness of agents (e.g., drugs, compounds, anti-cancer agents) on the expression or activity of Pin1. These and other agents are described in further detail in the following sections.

The present disclosure includes a method for detecting the presence or absence of monomeric Pin1 protein in a biological sample which may involve obtaining a biological sample from a test subject and contacting the biological sample with a compound or an agent capable of detecting monomeric Pin1 such that the presence of monomeric Pin1 may be detected in the biological sample. Any suitable agent for capable of detecting monomeric Pin1 may be employed. Suitable agents for detecting monomeric Pin1 may include any antibody capable of recognizing one or more protein modifications such as deacetylation of K13, deacetylation of K46, dephosphorylation of S16, desumoylation of K6, desumoylation of K63, phosphorylation of S65, phosphorylation of S138, and dephosphorylation of S71, among others.

An exemplary method for detecting the presence or absence of Pin1 protein or nucleic mutation in a biological sample may involve obtaining a biological sample from a test subject and contacting the biological sample with a compound or an agent capable of detecting Pin1 protein or a nucleic acid (e.g., mRNA, genomic DNA) that encodes Pin1 protein such that the presence of Pin1 protein or nucleic acid is detected in the biological sample. A preferred agent for detecting Pin1 mRNA or genomic DNA is a labeled nucleic acid probe capable of hybridizing to Pin1 mRNA or DNA. The nucleic acid probe may be, for instance, a Pin1 nucleic acid or a corresponding nucleic acid, such as oligonucleotide of a least 15, 30, 50, 100, 250 or 500 nucleotides in length which is capable of specifically hybridizing under stringent conditions to Pin1 mRNA or genomic DNA. Other suitable probes for use in the diagnostic assays of the disclosure are described here.

The immunological assay test samples of the present disclosure may include cells, protein or membrane extracts of cells, tissues, blood or biological fluids, such as ascites fluid or cerebrospinal fluid. The test sample used in the below-described method is based on the assay format, nature of the detection method and the tissues, cells or extracts used as the sample to be assayed.

In one embodiment, an agent for detecting Pin1 biomarker may be a primary antibody capable of binding to Pin1 protein. Primary antibodies may be polyclonal, or more preferably, monoclonal. An intact antibody, or a fragment thereof (e.g., Fab or F(ab')2) may be used. A secondary indirect antibody may be used to bind to the primary antibody. The secondary antibody may be conjugated with detection agents such as biotin or streptavidin.

With respect to antibody-based detection techniques, one of skill in the art may raise anti-Pin1 antibodies against an appropriate immunogen, such as isolated and/or recombinant Pin1 or a portion or fragment with specific modifications as described above (including synthetic molecules, such as synthetic peptides) using no more than routine experimentation. Synthetic peptides may be designed and used to immunize animals, such as rabbits and mice, for antibody production. The nucleic and amino acid sequence of Pin1 is known and may be used to design nucleic acid constructs for producing proteins for immunization or in nucleic acid detection methods or for the synthesis of peptides for immunization.

Conditions for incubating an antibody with a test sample may vary depending upon the tissue or cellular type. Incubation conditions may depend on the format employed in the assay, the detection methods employed, and the type and nature of the antibody used in the assay. One skilled in the art may recognize that any one of the commonly available immunological assay formats, such as radioimmunoassays, enzyme-linked immunosorbent assays, or immunofluorescent assays, may readily be adapted to employ a Pin1 antibody.

The detection method of the disclosure may be used to detect Pin1 mRNA, protein, or genomic DNA in a biological sample in vitro as well as in vivo. For example, in vitro techniques for detection of Pin1 mRNA may include northern blot hybridizations and in situ hybridizations. In vitro techniques for detection of Pin1 protein may include enzyme linked immunosorbent assays (ELISAs), Western blots, immunoprecipitations, immunofluorescence, or quantitative sequencing reactions. In vitro techniques for detection of Pin1 genomic DNA may include Southern hybridizations. The detection of genomic mutations in Pin1 (or other genes that effect Pin1 biomarker levels) may be used to identify inherited or somatic mutations.

Furthermore, in vivo techniques for detection of Pin1 protein may include introducing into a subject a labeled anti-Pin1 antibody. For example, the antibody may be labeled with a radioactive marker whose presence and location in a subject may be detected by standard imaging techniques.

In another embodiment, the biological sample may include Pin1 protein or nucleic acid from the test subject. In other embodiments, the methods further may involve obtaining a control biological sample from a control subject, contacting the control sample with a compound or agent capable of detecting Pin1 marker such that the presence of Pin1 marker is detected in the biological sample, and comparing the presence of Pin1 marker in the control sample with the presence of Pin1 marker in the test sample.

Methods for preparing protein extracts or membrane extracts of cells are well known in the art and may be readily be adapted in order to obtain a sample, which is compatible with the system utilized.

Pin1 biomarker diagnostic assays may also be carried out in subjects diagnosed or at risk of a proliferative disorder, such as cancer. In other embodiments, Pin1 biomarker diagnostic assays may be also carried out in subjects diagnosed or at risk of an inflammatory disease, such as asthma, lupus, among others. In yet another embodiment, Pin1 biomarker diagnostic assays may be also carried out in subjects diagnosed or at risk addiction, such as cocaine addiction, among others.

Experimental Results

Effect of SIRT1 in Pin1 Deacetylation

FIG. 1 depicts HTS results for glucose starvation induced Pin1 deacetylation in cells 100. Different stress tests, such as heat shock, ultraviolet radiation, and glucose starvation (Glu$^-$), may produce an extracellular stimulus that could transform one or more cellular responses related to cell growth, differentiation, activation of transcript factors, glucose metabolism, control of proteins synthesis, and regulation of cell cycle. Among these stresses testes, glucose starvation (Glu$^-$), may reduce Pin1 acetylation without affecting its protein expression (FIG. 1 A). A mimicking glucose starvation with 2-deoxyglucose (2-DG), a glucose analog, may be used to cause reduction in Pin1 acetylation in a time- or dose-dependent manner (FIG. 1 B). Protein acetylation may be catalytically modulated by a particular pair of histone acetyl transferase (HAT) and histone deacetylase (HDAC) (Yang and Seto, 2007). To identify the HAT and HDAC that modulates Pin1 acetylation, Flag-tagged Pin1 was expressed with several HATs including p300, CBP or GCN5 in cells, followed by co-immunoprecipitation (Co-IP) with anti-Flag antibody and immunoblotting with anti-acetyl lysine antibody. Acetyl-Pin1 was significantly increased when p300 was overexpressed (FIG. 1 C), which was reversed by two p300 inhibitors, Garcinol (Gar) and Anacardic acid (AnAc) (FIG. 1 D). Moreover, Pin1 Co-IPed with p300, supporting that p300 is a HAT for Pin1. For the corresponding HDAC, various HDAC inhibitors targeting different HDAC categories were used, including Trichostatin A (TSA) and MS-275 for class I and II HDACs as well as Nicotinamide (NAM) and Splitomicin (Splito) for class III HDACs. NAM and Splito, but not others, increased Pin1 acetylation (FIG. 1 E), thus suggesting that Pin1 HDACs belong to Class III HDACs comprised of the Sirtuin family.

Out of the seven Sirtuin family members, SIRT1, 2, 6, and 7 associated with Pin1 as shown by Co-IP and GST pull-down (FIG. 1 F). However, only SIRT1 reduced Pin1 acetylation (FIG. 1 G). Furthermore, overexpression of wild-type (WT), but not its catalytic dead (H363Y) mutant, induced Pin1 deacetylation in cells (FIG. 1 H). Moreover, Pin1 acetylation was significantly elevated in SIRT1 KO MEFs, which was reversed by re-constitution of WT-SIRT1 (FIG. 1 I). In addition, since other studies have shown that glucose starvation activates SIRT1 activity, an investigation was made to know whether glucose starvation-induced Pin1 deacetylation is mediated by SIRT1. The results showed that 2-DG-induced Pin1 deacetylation was suppressed in SIRT1 KD cells, which was rescued by over-expressing SIRT1, but not its dead mutant (FIG. 1 J). Pin1 also exhibited increased binding with SIRT1 upon glucose starvation or 2-DG treatment, as shown by Co-IP (FIG. 1 K), and co-immunostaining (FIG. 1 L). Thus, these data demonstrate that activation of SIRT1 increases Pin1 deacetylation.

Effect of Deacetylation at K13 and K46 Residues in Pin1 Activity

FIG. 2 depicts the effect of deacetylation at K13 and K46 residues in Pin1 activity 200. As SIRT1 deacetylates Pin1, a map of the corresponding acetylation residues in Pin1 may be created. By analyzing Pin1 domains, it was found that acetylation occurred in the N-terminal WW domain that contains three lysine residues, K6, K13 and K46 (FIG. 2 A). Mutation of K13 or K46, but not K6, partially reduced Pin1 acetylation, while double mutation K13/46R completely abolished Pin1 acetylation, indicating that acetylation likely occurs of K13 and K46 (FIG. 2 B), two highly evolutional conserved Lys residues (FIG. 2 C). Indeed, it was confirmed K13 and K46 acetylation of Pin1 by mass spectrometry (FIGS. 2 D and E).

To investigate the effects of these two acetylation residues on Pin1 activity, the ability of Pin1 to bind MPM2 antigens, well-documented Pin1 substrates in mitotic cells was examined. GST-Pin1 and its acetylation-mimicking variant, GST-K13/46Q (2Q), or acetylation-resistant variant, GST-K13/46R (2R) were purified and incubated with mitotic extracts, followed by GST pulldown assay. As compared with WT GST-Pin1, GST-2Q, but not GST-2R, displayed a greatly impaired ability to bind MPM2 antigens (FIG. 2 F), suggesting that Pin1 acetylation might reduce its substrate-binding activity. To support these results, Pin1 substrate binding and function in SIRT1 KD cells was examined. When Pin1 acetylation was increased by SIRT1 KD, Pin1 exhibited reduced ability to bind to MPM2 antigens (FIG. 2 G) or to stabilize its substrates including HER2 and Cyclin D1 (FIG. 2 H). SIRT1 KD also increased Pin1 protein turnover (FIGS. 2 I and J). Thus, in addition to enhancing Pin1 substrate binding, SIRT1-medidated Pin1 deacetylation increases its protein levels.

To further support this finding and based on the fact that Pin1 is highly expressed in human cancers including breast cancer, whether SIRT1 is also overexpressed and correlated with Pin1 expression in human breast cancer cell lines and tissues was examined. Out of selected cell lines examined, the two molecules were expressed at low levels in the immortalized non-transformed cells HMLE and MCF10A, but at high levels in transformed cell lines. This correlation was further validated by analyzing Pin1 and SIRT1 using immunohistochemistry on normal and cancerous breast tissue arrays. Whereas both SIRT1 and Pin1 were low in all 24 human normal breast tissues, they were overexpressed and highly correlated with each other in 65 human breast cancer tissues (P value=$7.43 \times 10^{-23}$). These results demonstrated that Pin1 expression is strongly correlated with SIRT1 in human breast cancer tissues and cells, further supporting the importance of SIRT1-mediated deacetylation of Pin1.

To investigate the molecular impact of SIRT1-mediated deacetylation of Pin1, the spatial distribution of K13 and K46 in the Pin1 crystal structure was examined and it was found that Pin1 existed as a dimer, briefly mentioned (Ranganathan et al., 1997), but has never been appreciated in the past years. Moreover, both K13 and K46 locate in the interface of the Pin1 dimer. To verify if the Pin1 dimer exists in vivo and is regulated by SIRT1-mediated deacetylation, Co-IP and crosslinking experiments were performed. Flag-Pin1 Co-IPed with HA-Pin1 or GFP-Pin1 in cells (FIGS. 2 K and L), was completely abolished by overexpressing SIRT1, but not its inactive H363Y mutant (FIG. 2 L). Moreover, when cell extracts were treated with the chemical crosslinker EGS before Co-IP, a shifted dimer signal on Flag-Pin1 was readily detected (FIG. 2 M). As compared with wild-type Pin1, the acetylation-mimicking 2Q mutant increased dimer formation, whereas the acetylation-resistant 2R mutant formed no detectable dimer (FIG. 2 N).

Molecular modeling provided the structural basis for Pin1 dimerization. In the native Pin1 dimer structure (Ranganathan et al., 1997), the backbone of K46 from one Pin1 monomer formed two water-mediated hydrogen bonds with the carboxylic side chain of E100 from the other Pin1 monomer (FIG. 2 O, left panel). However, acetylation of K46 leads to the elongation of its side chain toward E101 and D102, to form additional hydrogen bonds, thereby strongly favoring Pin1 dimerization (FIG. 2 O, right panel). Both biochemical and structural results consistently support that Pin1 acetylation favors dimer formation, while SIRT1-mediated deacetylation keeps Pin1 in a monomeric state, therefore increases Pin1 activity.

Effect of Cancer-Derived Pin1 Mutations, Q33K and E100D in Pin1 Activity

FIG. 3 depicts test results for Q33K and E100D mutations in Pin1 activity 300. In order to evaluate the clinical relevance of the Pin1 monomer in human cancers, five Pin1 mutations (Q33K, E100D, E145K, G148R, and P149S) were searched in the cBio Cancer Genomics Portal and the COSMIC database and their oncogenic activity was examined (FIG. 3 A). Among them, the Q33K and E100D Pin1 mutants were notably more active than WT protein in activating the cyclin D1 promoter (FIG. 3 B), and in binding to the Pin1 substrate MPM2 antigens, indicators for Pin1 in vivo activity. Furthermore, MDA-MB-231 cells stably expressing the Q33K or E100D mutant displayed increased proliferation (FIG. 3 C) and generate more foci in colony forming assays (FIG. 3 D). Moreover, Q33K or E100D mutations prevented Pin1 dimer formation (FIG. 3 E).

E100 localizes to the interface of the Pin1 dimer and binds to K46 (FIG. 3 I, Left panel). However, the distance of a water-mediated hydrogen bonds between E100D and K46 was significantly longer (3.9 Å) than E100 and K46 in WT Pin1 (2.5 Å) (FIG. 3 I, Right panel), favoring Pin1 monomer and enhancing Pin1 tumorigenic activity. However, in FIG. 3 J, molecular modeling analysis was performed by imposing two energy-minimized monomeric Q33K forms on the dimer structure, where Q33K was located in the center of the Pin1 dimer without interacting with any lysine residues of the interface. The closest residue to Q33K was another Q33K from the other half of the dimer and the distance between the two positive charges of K33 was 4.1 Å, much shorter than that between two Q33 in WT Pin1, which is normally 12.0 Å (FIG. 3 J). In such a short distance, two positive charges would repel each other, keeping Pin1 in a monomeric state. Thus, both cancer-derived Q33K and E100D mutations favor the active Pin1 monomer and enhance Pin1 oncogenic activity.

Given that the Q33K or E100D mutation keeps Pin1 in the constitutively active monomer, their structural basis in the Pin1 dimer structure was examined. As shown in FIG. 2 O, E100 localizes to the interface of the Pin1 dimer and binds to K46. However, the distance of one of the water-mediated hydrogen bonds between E100D and K46 (3.9 Å) was significantly longer than the WT one between E100 and K46 (2.5 Å) (FIG. 3 I), thus favoring Pin1 monomer and enhancing Pin1 tumorigenic activity. To corroborate this hypothesis, the E100A mutant was done and found that like E100D Pin1, the E100A mutant displayed increased activity to bind to Pin1 substrates MPM2 antigens (FIG. 3 F) and to promote foci formation (FIG. 3 G).

According to the results, the Q33K mutation was located in the center of the Pin1 dimer without interacting with any lysine residues of the interface. Molecular modeling analysis was carried out by imposing two energy-minimized monomeric Q33K forms on the dimer structure. The closest residue to Q33K is another Q33K from the other half of the dimer. The distance between two positive charges of K33 was 4.1 Å, much shorter than that between two Q33 in WT Pin1, which is normally 12.0 Å (FIG. 3 J). In such a short distance, two positive charges would repel each other and keep Pin1 in a monomeric state. This model is supported as it was revealed that the charge is essential for Q33K in enhancing Pin1 activity; Q33R mutant carrying a positive charge, but not Q33L, behaved similar to Q33K in increasing Pin1 activity (FIG. 3 H) and oncogenic property (FIG. 3 G). Thus, both cancer-derived Q33K and E100D mutations favor the active Pin1 monomer and enhance Pin1 oncogenic activity.

This invention is further illustrated by the following examples which should not be construed as limiting. The following examples show the use of Pin1 as a universal biomarker for abnormal cell growth, e.g., cancer and the involvement of Pin1 in tumorigenic pathways.

EXAMPLES

Example 1—Pin1 is a Breast Tumor Biomarker

To determine whether Pin1 is overexpressed in human tumor samples, it was examined the levels of Pin1 in human breast cancer samples using immunoblotting and immunohistochemical analysis with Pin1 antibodies, as described previously by Lu et al. (1999) and Liao et al. (2009).

Immunocytochemistry of sections of human breast tumors showed that Pin1 is indeed overexpressed in human breast tumor cells. Pin1 was detected both in the cytoplasm and in the nucleus, as well as in condensed chromosomes and mitotic spindles. Infiltrating carcinoma cells were strongly positive for Pin1 staining, while surrounding normal connective tissue, blood vessels, adipose, and stromal cells were only weakly positive. To ensure that these signals represent Pin1, a control immunostaining was performed whereby the Pin1-specific antibodies were first specifically depleted by pre-incubation with glutathione beads containing GST-Pin1. This depletion resulted in no detection of signal, demonstrating the specificity of the Pin1 antibodies used in the immunostaining. Furthermore, similar immunostaining in various breast tumor-derived cell lines, when compared with those in non-transformed mammary cell lines, showed significantly elevated expression of Pin1 (Wulf et al., 2001).

Example 2—Pin1 is a Colon Tumor Biomarker

To explore whether Pin1 is also overexpressed in colon tumors, it has been examined the Pin1 levels in several human colon tumor samples using immunostaining and immunoblotting analyses (using the experimental methods set forth in Example 1). Pin1 was overexpressed in most of the samples examined, as compared with normal colon samples. These results indicate that Pin1 may act as biomarker for colon cancer.

Example 3—Pin1 as a Prostate Tumor Biomarker

To explore whether Pin1 is also overexpressed in prostate tumors, the Pin1 levels in several human prostate tumor samples were tested using immunostaining and immunoblotting analyses (using the experimental methods set forth in Example 1). Pin1 was overexpressed in most of the samples examined, as compared with normal prostate samples. These results indicate that Pin1 may act as biomarker for prostate cancer.

Example 4—Pin1 is a Universal Biomarker of Proliferation

To further evaluate the potential of detecting Pin1 levels as a general biomarker for cell proliferation, the expression of Pin1 in an array of normal human tissues was assessed. A panel of 30 normal human tissues was stained with affinity-purified anti-Pin1 antibodies. Although very low levels of Pin1 were detected in non-epithelial cell types, such as different kinds of muscles, Pin1 was primarily detected at moderate levels in various types of epithelial cells, hemopoietic cells and at very high levels in germline cells of testis and ovary, especially in sperm. Specifically, it was observed that Pin1 expression in normal human tissues was associated with proliferative status. For instance, cell proliferation primarily occurs at the base portion of clefts in colon and they stop proliferation when they move up along the cleft. In such areas, a gradient in the level of Pin1 signal was observed, e.g., Pin1 levels were much higher in the base portion than that in upper portion of clefts in colon. Similar-phenomena were also observed in other tissues, such as the transitional epithelial cells of bladder. With the exception of testis, Pin1 levels in normal human tissues are much lower than those observed in human breast or prostate tumor samples. These results further indicate that detection of Pin1 levels may be used as a diagnostic biomarker for abnormal proliferation in an array of human tissues and diseases.

While various aspects and embodiments have been disclosed, other aspects and embodiments are contemplated. The various aspects and embodiments disclosed are for purposes of illustration and are not intended to be limiting, with the true scope and spirit being indicated by the following claims.

The invention claimed is:

1. A method of treating a proliferative or immune disorder in a subject, said method comprising:
   (a) obtaining a sample from said subject;
   (b) determining whether an aberrant mutation is present in the gene encoding Pin1 in said sample; and
   (c) treating said subject with a retinoic acid compound if at least one of said aberrant mutations is present;
   wherein said aberrant mutation encodes an amino acid substitution in Pin1 selected from: Q33K or E100D.

2. The method of claim 1, wherein said step of determining whether an aberrant mutation is present comprises sequencing all or a portion of the Pin1 gene.

3. The method of claim 1, wherein said step of determining whether an aberrant mutation is present comprises contacting said sample with a nucleic acid probe specific for Pin1.

4. The method of claim 3, wherein said probe is bound to a microarray.

5. The method of claim 1, said method further comprising determining whether an aberrant post-translational modification of Pin1 is present and treating said subject with a retinoic acid compound if at least one of said aberrant post-translational modifications is present, wherein said post-translational modification is selected from the group consisting of deacetylation of K13, deacetylation of K46, dephosphorylation of S16, desumoylation of K6, desumoylation of K63, phosphorylation of S65, phosphorylation of S138, and dephosphorylation of S71.

6. The method of claim 1, wherein said disorder is a proliferative disorder.

7. The method of claim 1, wherein said disorder is an immune disorder.

8. The method of claim 1, wherein said retinoic acid compound is part of a pharmaceutical composition formulated for long-term delivery of said retinoic acid compound after injection of said composition into said subject.

9. The method of claim 8, wherein said composition is formulated as an injectable depot system, an injectable drug suspension, an injectable microsphere, or an injectable gel.

10. The method of claim 9, wherein said injectable drug suspension is:
    (a) an oil-based suspension,
    (b) formulated for intravenous injection or intramuscular injection,
    (c) formulated as an injectable gel and for intramuscular injection,
    (d) formulated to delay the metabolism of said retinoic acid compound,
    (e) further comprises a pharmaceutically acceptable excipient, or
    (f) said retinoic acid compound is all-trans retinoic acid.

11. The method of claim 1, wherein said retinoic acid compound is all-trans retinoic acid.

12. A method of treating a proliferative or immune disorder in a subject, wherein said subject has an aberrant mutation in the gene encoding Pin1 that produces an amino acid substitution selected from Q33K or E100D, said method comprising administering a retinoic acid compound to said subject.

13. The method of claim 12, wherein said Pin1 further comprises an aberrant post-translational modification selected from the group consisting of deacetylation of K13, deacetylation of K46, dephosphorylation of S16, desumoylation of K6, desumoylation of K63, phosphorylation of S65, phosphorylation of S138, and dephosphorylation of S71.

14. The method of claim 12, wherein said disorder is a proliferative disorder.

15. The method of claim 12, wherein said disorder is an immune disorder.

16. The method of claim 12, wherein said retinoic acid compound is all-trans retinoic acid.

17. A method of treating a proliferative or immune disorder in a subject, said method comprising:
    (a) obtaining a sample from said subject;
    (b) determining whether an aberrant post-translational modification of Pin1 is present; and
    (c) treating said subject with a retinoic acid compound if at least one of said aberrant post-translational modifications is present;
    wherein said post-translational modification is selected from deacetylation of K13 or aRet deacetylation of K46.

18. The method of claim 17, said method further comprising determining whether a further aberrant post-translational modification of Pin1 is present and treating said subject with a retinoic acid compound if at least one of said further aberrant post-translational modification is present, wherein said post-translational modification is selected from the group consisting of dephosphorylation of S16, desumoylation of K6, desumoylation of K63, phosphorylation of S65, phosphorylation of S138, and dephosphorylation of S71.

19. The method of claim 17, wherein said retinoic acid compound is all-trans retinoic acid.

20. The method of claim 17, wherein said disorder is a proliferative disorder.

21. The method of claim 17, wherein said disorder is an immune disorder.

22. A method of treating a proliferative or immune disorder in a subject, wherein said subject has an aberrant post-translational modification of Pin1 selected from deacetylation of K13 or deacetylation of K46, said method comprising administering a retinoic acid compound to said subject.

23. The method of claim 22, wherein said Pin1 further comprises an aberrant post-translational modification selected from the group consisting of dephosphorylation of S16, desumoylation of K6, desumoylation of K63, phosphorylation of S65, phosphorylation of S138, and dephosphorylation of S71.

24. The method of claim 22, wherein said disorder is a proliferative disorder.

25. The method of claim 22, wherein said disorder is an immune disorder.

26. The method of claim 22, wherein said retinoic acid compound is all-trans retinoic acid.

* * * * *

UNITED STATES PATENT AND TRADEMARK OFFICE
CERTIFICATE OF CORRECTION

PATENT NO. : 10,351,914 B2  
APPLICATION NO. : 15/326981  
DATED : July 16, 2019  
INVENTOR(S) : Kun Ping Lu et al.

Page 1 of 1

It is certified that error appears in the above-identified patent and that said Letters Patent is hereby corrected as shown below:

In the Claims

Column 22, Claim 17, Line 27, replace "from deacetylation of K13, or aRet deacetylation of K46." with --from deacetylation of K13 or deacetylation of K46.--

Signed and Sealed this  
Sixteenth Day of February, 2021

Drew Hirshfeld  
*Performing the Functions and Duties of the*  
*Under Secretary of Commerce for Intellectual Property and*  
*Director of the United States Patent and Trademark Office*